US005789754A

United States Patent [19]
Cathey et al.

[11] Patent Number: 5,789,754
[45] Date of Patent: Aug. 4, 1998

[54] LEAK DETECTION METHOD AND APPARATUS FOR PLASMA PROCESSING EQUIPMENT

[75] Inventors: David A. Cathey; Rodney C. Langley, both of Boise, Id.

[73] Assignee: Micron Technology, Inc., Boise, Id.

[21] Appl. No.: 699,489

[22] Filed: Aug. 19, 1996

[51] Int. Cl.$^6$ .................................. G01N 21/73
[52] U.S. Cl. ............................................. 250/372
[58] Field of Search ................................ 250/372

[56] References Cited

U.S. PATENT DOCUMENTS 5,326,975  7/1994  Barna ............................. 250/372

*Primary Examiner*—Constantine Hannaher
*Attorney, Agent, or Firm*—Wells, St. John, Roberts, Gregory & Matkin, P.S.

[57] ABSTRACT

In one aspect, a method of detecting leaks of external atmospheric gases into a plasma reactor comprises monitoring an emission spectra of a plasma within the reactor for the presence of an external atmospheric constituent. In another aspect, a method of detecting an external atmospheric leak in a plasma enhanced reactor comprising detecting photon emission of excited nitrogen present within the reactor. In yet another aspect, a leak detection system of continuously detecting for leaks of external atmospheric gases into a plasma reactor comprises: a) an optical detection apparatus in optical communication with a plasma in the plasma reactor; b) the optical detection apparatus being configured to monitor an emission spectra of the plasma for a signal due to presence of an external atmospheric constituent within the plasma and for a signal due to a non-atmospheric constituent within the plasma; and c) an alarm configured to generate a response when the relative size of the external atmospheric constituent signal to the non-atmospheric constituent signal exceeds a predetermined value.

1 Claim, 3 Drawing Sheets

LEAK DETECTION METHOD AND APPARATUS FOR PLASMA PROCESSING EQUIPMENT

TECHNICAL FIELD

The invention pertains to methods for leak detection in plasma reactors, and specifically pertains to methods for detecting leakage of atmosphere into a plasma reactor.

BACKGROUND OF THE INVENTION

A prior art plasma reactor 10 is described with reference to FIG. 1. Plasma reactor 10 comprises a reactor vessel 12 having ports 14 and 16 therethrough. Port 14 opens to a gas inlet 18, and port 16 opens to a gas outlet 20.

Within reactor vessel 12, a plasma 26 is generated. Plasma 26 creates a glow discharge. The glow discharge results from excited atoms and molecules within the plasma emitting photons as they relax from excited states to lower states. The photons emitted have wavelengths characteristic of the atoms and molecules from which they are discharged. Accordingly, the constituents of a plasma can be ascertained by monitoring the photons of the glow discharge and ascertaining the wavelengths of the photons.

Preferably, vessel 12 will comprise a window 22 configured for allowing passage of photons therethrough, with window 22 being in optical communication with optical detection hardware 24. Optical detection hardware 24 is preferably coupled to a spectrum analyzer 25, with the detection hardware 24 and spectrum analyzer 25 together being configured to detect the relative wavelengths and intensities of photons emitted from plasma 26 and to generate a spectrum 28 wherein intensity is plotted against wavelength. Spectrum 28 will comprise peaks 30 characteristic of the atoms and molecules within plasma 26.

Optical detector 24 may comprise any of a number of configurations known to persons of skill in the art, including, for example, a diffraction grating with a photomultiplier tube, a prism with a photomultiplier tube, and a prism with a pin-diode array photocell. Optical detectors and spectrum analyzers suitable for use in the shown system may be purchased from a number of suppliers, including, for example, XINIX.

The general prior art purpose of the optical detection hardware is to determine when a semiconductor processing step is substantially complete. For instance, if the processing step is an etch of a first material from over a second material, the optical detection hardware 24 can be utilized to determine when the relative amount of first material within plasma 26 begins to decrease and the relative amount of second material begins to increase. At this point, the etch is beginning to penetrate into the second material, and the process will generally be determined to be substantially completed.

The relative abundance of a material within plasma 26 can be determined by monitoring the intensity of a peak corresponding to that material relative to the intensities of other peaks within the spectrum 28. The intensity of a given peak will be proportional to the amount of its corresponding material within the plasma 26.

A problem with plasma reactors, is that occasionally a leak 40 will develop in the reactor vessel 12 and external atmosphere (shown as arrows entering vessel 12 in the vicinity of leak 40) will enter vessel 12. Such atmosphere within the vessel is undesired as components of the atmosphere will be incorporated into plasma 26 and will disrupt the chemical properties of plasma 26. In processes requiring high precision, such as semiconductor processing, such disruption of the chemical properties of the plasma is undesired as it will affect processing and reduce tolerances achieved by the processing. Accordingly, it is desired to detect leaks in the reactor vessel 12.

BRIEF DESCRIPTION OF THE DRAWINGS

Preferred embodiments of the invention are described below with reference to the following accompanying drawings.

SUMMARY OF THE INVENTION

The invention provides methods and apparatus for detecting leaks of atmospheric gases into a plasma reactor.

In one aspect, the invention provides a method for detecting leaks of external atmospheric gases into a plasma reactor. In one implementation, the method is performed by monitoring an emission spectra of a plasma within the reactor for the relative abundance of an external atmospheric constituent. For example, in one exemplary implementation, the method may be implemented to detect photon emission of excited nitrogen within the reactor. An exemplary apparatus in accordance with the invention may include an optical detection apparatus in optical communication with a plasma in the plasma reactor. The optical detection apparatus will be configured to monitor an emission spectra of the plasma for a signal indicative of the presence of an external atmospheric constituent within the plasma, and to generate a signal indicative thereof. In one exemplary implementation, the system may include an alarm operated to generate a response when the monitored size of the external atmospheric constituent signal reaches a selected value.

DESCRIPTION OF SPECIFIC EMBODIMENTS

Figure 1:
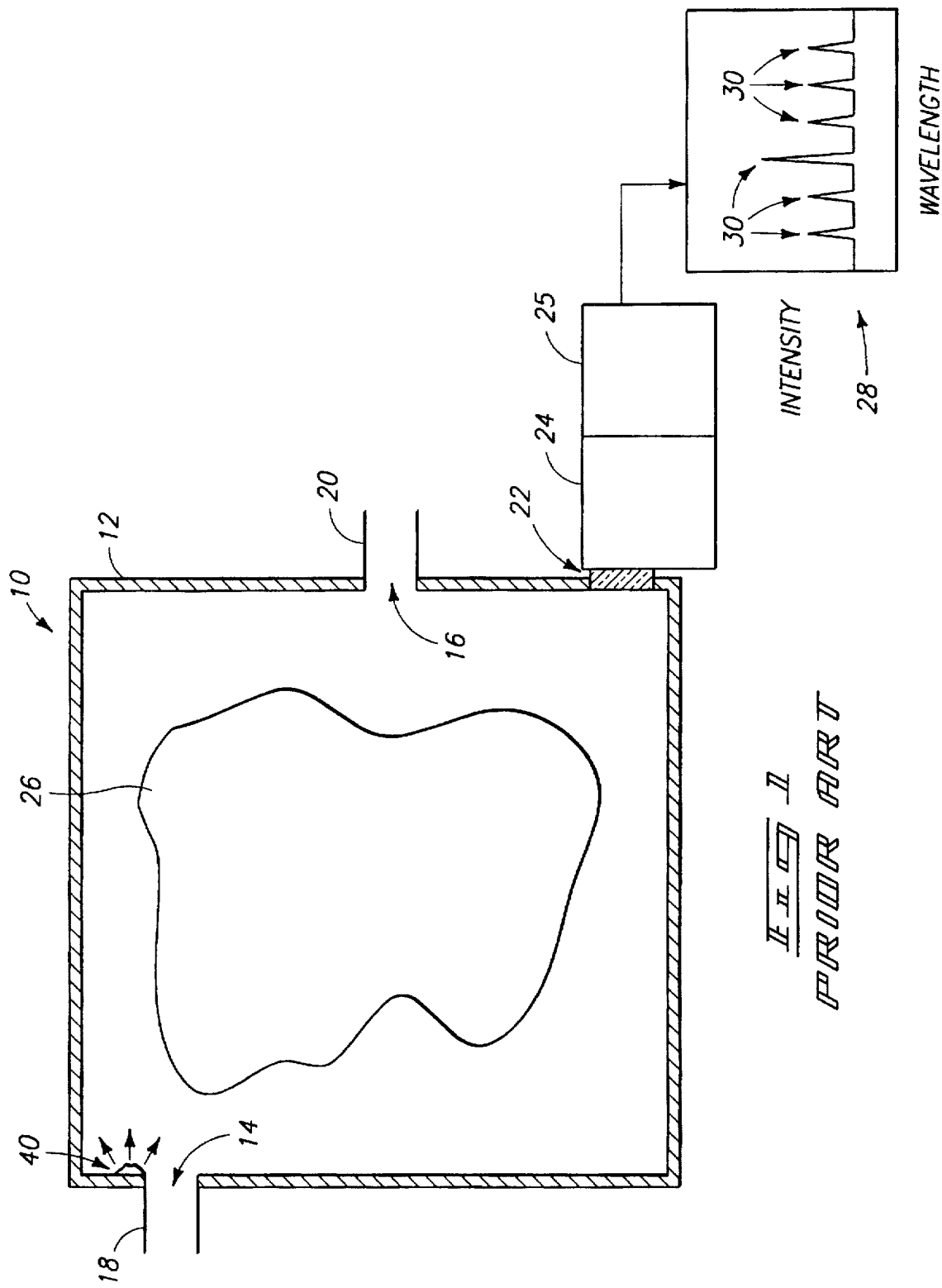
FIG. 1 is a cross-sectional diagrammatic view of a prior art plasma reactor.
Figure 2:
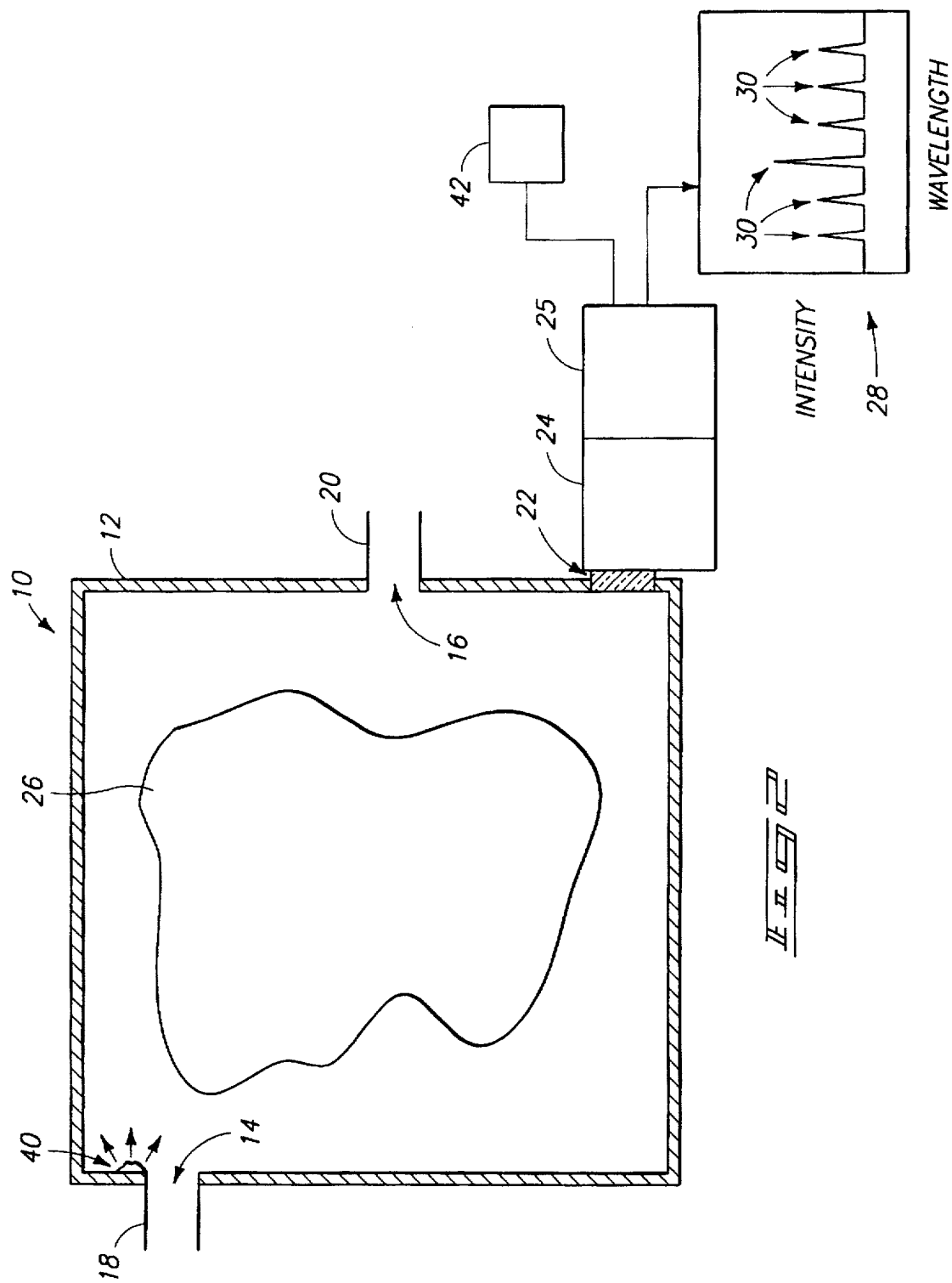
FIG. 2 is a cross-sectional diagrammatic view of plasma reactor modified according to the method of the present invention.

A preferred embodiment of the invention is described with reference to FIG. 2, wherein the prior art plasma reactor 10 of FIG. 1 is illustrated as modified according to the present invention. Specifically, an alarm 42 is electrically coupled, through spectrum analyzer 25, to the optical detector 24. Alarm 42 is configured to generate a signal in response to optical detector 24 detecting a predetermined peak indicative of an atmospheric leak, i.e., a leak-indicative peak. Preferably, detector 24 will be configured to detect signals within a range of from about 280 nanometers to about 800 nanometers, a range which encompasses many leak-indicative peaks. Also preferably, alarm 42 will generate the signal in response to the leak-indicative peak exceeding a predetermined threshold value, and, preferably, the signal generated by alarm 42 will be detectable by technicians monitoring the reactor 10. Example technician detectable signals are audible signals and visible signals.

As discussed below, the present invention can provide for relatively continuous monitoring for atmospheric leaks into a plasma reactor. The alarm 42 and optical detector 24 can be configured for automatic signaling when there is an atmospheric leak of substantial proportion into reactor vessel 12.

As discussed previously, any atom or molecule present in plasma 26 will emit photons at wavelengths characteristic of the particular atom or molecule. Accordingly, every external atmospheric constituent will have a characteristic spectral pattern associated with it. For instance, nitrogen gas (dinitrogen), which makes up about 80% of the atmosphere external to the reactor, has a spectral peak located at 337.1 nanometers. Thus, when the desired plasma does not comprise nitrogen; one method for configuring optical detector 24, spectrum analyzer 25, and alarm 42 for indicating an atmospheric leak is to configure alarm 42 to generate a signal when a peak at 337.1 nanometers exceeds a predetermined threshold value.

It is noted, however, that there can be problems associated with simply detecting the intensity of a single peak, such as the above-mentioned 337.1 nanometer dinitrogen peak. For instance, window 22 may become fogged or clouded during continuous exposure to plasma 26. Accordingly, the sensitivity of optical detector 24 to a given quantity of dinitrogen in reactor vessel 12 can diminish over time. Thus, at later times in an extended use period of a plasma reactor, an equal intensity of a dinitrogen peak at 337.1 nanometers can indicate more dinitrogen in plasma vessel 12 than was indicated at earlier times. In other words, it can take increasingly more dinitrogen to reach a predetermined level and trigger alarm 42 at later times as compared to earlier times. Thus, unless alarm 42 is continuously recalibrated for changes in sensitivity of detector 24, undesirably large quantities of atmosphere can enter reaction chamber 12 before alarm 42 is triggered. In a semiconductor processing application, this could undesirably allow several wafers to be ruined before alarm 42 activates.

Because of the potential changes in sensitivity of detector 24 over time, it is preferable to determine the relative intensity of an external-atmosphere-constituent indicative peak to a non-external-atmosphere-constituent indicative peak, rather than determining the absolute intensity of an external-atmosphere-constituent indicative peak. For instance, in the above-discussed example where the 337.1 nanometer dinitrogen peak is detected, it is preferable to compare the intensity of this peak to the intensity of a plasma-constituent peak, such as a 603.2 nanometer peak characteristic of argon, a typical plasma component. The plasma-constituent peak will be present regardless of whether atmosphere is leaking into reactor 12. The relative intensity of the dinitrogen peak to the argon peak will increase when atmosphere leaks into vessel 12, regardless of the amount of fogging on window 22. Thus, alarm 42 is preferably configured to respond when the relative ratio of an atmospheric constituent to a non-atmospheric constituent increases beyond a predetermined threshold value. The increase in such relative ratio can be ascertained by the relative intensity of atmosphere-constituent indicative peak to a non-atmosphere-constituent indicative peak.

Although dinitrogen is discussed as an example atmospheric constituent which can be monitored, any other atmospheric constituent could also be monitored. Such other atmospheric constituents include oxygen gas (dioxygen) and carbon dioxide, for example. Also, although argon is discussed above as an example of a plasma constituent, the presence of which could be monitored, the presence of other plasma constituents could also be monitored. The particular plasma constituents will vary on the application of reactor 12, some typical constituents being, for example, fluorocarbons.

Figure 3A:
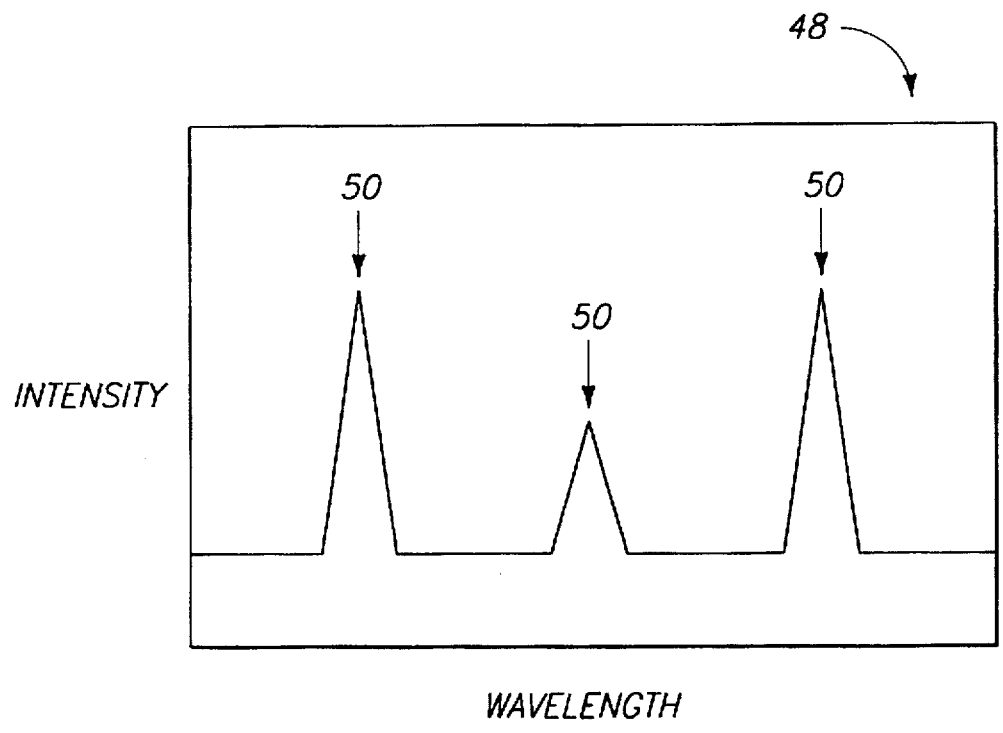
FIG. 3 is a representation of a minimum-atmospheric-leakage peak distribution in an emission spectrum (FIG. 3A) compared to a substantial-atmospheric-leakage peak distribution in an emission spectrum (FIG. 3B).
Figure 3B:
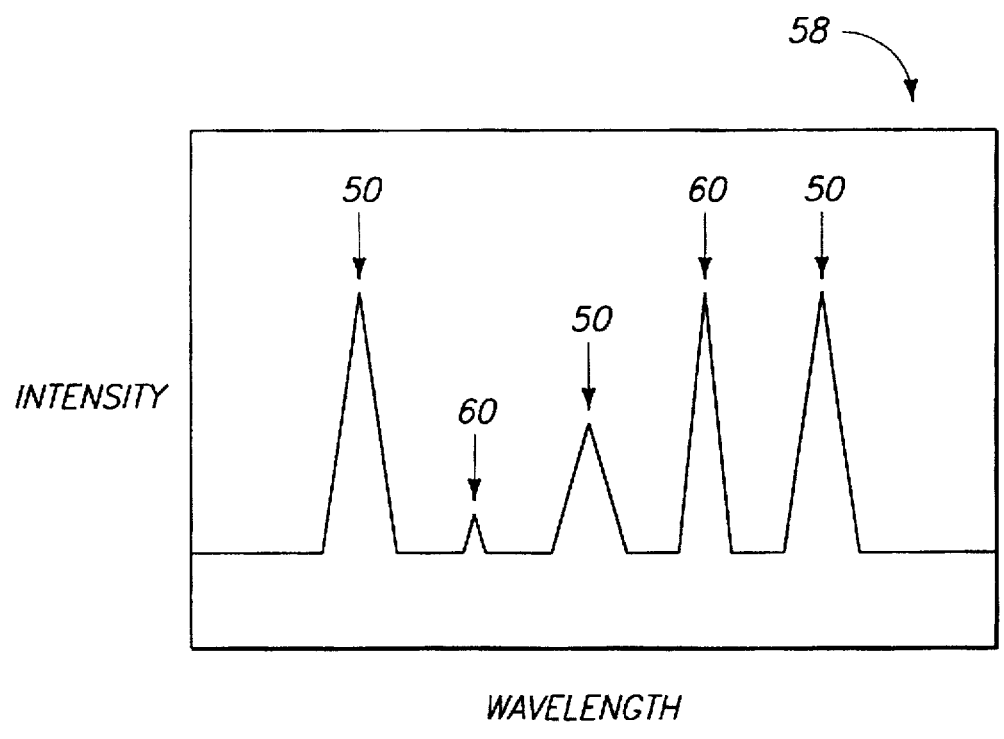

In a further aspect of the invention, the spectral locations of particular atmospheric-constituent peaks are not necessarily previously known. Rather, external atmosphere can be introduced into the plasma, and the spectral location of atmospheric-constituent peaks can be experimentally determined. The method is described with reference to FIG. 3. In FIG. 3A is illustrated a figurative spectrum 48 obtained of a plasma from within plasma reactor with little or no external atmosphere being present. Accordingly, spectrum 48 comprises a minimum-atmospheric-leakage peak distribution, with peaks 50 corresponding to constituents of the plasma. The spectrum 48 is for example purposes only, and does not necessarily correspond to a spectrum which would actually be obtained from a plasma reactor.

After the spectrum 48 is obtained, atmospheric gases can be purposely introduced into a plasma 26 to generate a spectrum 58 (shown in FIG. 3B) with a peak distribution corresponding to a plasma after there has been substantial atmospheric leakage. Accordingly, spectrum 58 comprises a substantial-atmospheric-leakage peak distribution. Spectrum 58 will comprise a spectrum of peaks 60 due to atmospheric constituents superimposed on the peaks 50 due to plasma components. The peaks 60 are leak-indicative peaks, which are substantially absent in the minimum-atmospheric-leakage peak distribution of spectrum 48. The spectrum 58 is shown for example purposes only, and does not necessarily correspond to a spectrum obtained after atmospheric gases are introduced into a plasma reactor. The external atmosphere gases may be introduced into plasma 26 by bleeding atmospheric gases into the reaction vessel 12 through a bleed port (not shown).

Once that it is ascertained where one or more leak-indicative peaks will appear in a spectrum, atmospheric gases can be removed from the plasma. Such removal can be accomplished, for instance, by allowing time in the reactor for the atmospheric gases to be expelled through outlet 20. Another example process for removing the atmospheric gases from the reactor is to extinguish the plasma 26 and exhaust the plasma components from reactor vessel 12, and then to reestablish plasma 26 within the reactor vessel.

Once the atmospheric gases are removed from the plasma, the spectrum of the plasma glow discharge can be monitored for the presence of a leak-indicative peak. Preferably, the spectrum will be monitored for a ratio of an intensity of a leak-indicative peak 60 to the intensity of a plasma constituent peak 50.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method of detecting leaks of external atmospheric gases into a plasma reactor comprising:

establishing a plasma inside the plasma reactor; and monitoring an emission spectra of said plasma within the reactor for the presence of an external atmospheric constituent indicative of a leak, the external atmospheric constituent being oxygen gas.

* * * * *